United States Patent
Sawa

(10) Patent No.: US 8,658,703 B2
(45) Date of Patent: Feb. 25, 2014

(54) AQUEOUS SUSPENSION PREPARATIONS

(75) Inventor: Shirou Sawa, Hyogo (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 648 days.

(21) Appl. No.: 12/484,636

(22) Filed: Jun. 15, 2009

(65) Prior Publication Data

US 2009/0253807 A1    Oct. 8, 2009

Related U.S. Application Data

(62) Division of application No. 10/362,473, filed as application No. PCT/JP01/07128 on Aug. 20, 2001, now abandoned.

(30) Foreign Application Priority Data

Aug. 25, 2000 (JP) .................. 2000-255000

(51) Int. Cl.
*A61K 47/32* (2006.01)

(52) U.S. Cl.
USPC ...................................... 514/772.5

(58) Field of Classification Search
USPC ...................................... 514/772.5
See application file for complete search history.

(56) References Cited

U.S. PATENT DOCUMENTS

| | | | |
|---|---|---|---|
| 2,731,387 A * | 1/1956 | Auhagen et al. | 514/192 |
| 4,914,090 A | 4/1990 | Watkins | |
| 5,192,535 A | 3/1993 | Davis et al. | |
| 5,626,879 A | 5/1997 | Anaebonam et al. | |
| 5,670,171 A | 9/1997 | Santus et al. | |
| 5,679,665 A | 10/1997 | Bergamini et al. | |
| 5,696,101 A | 12/1997 | Wu et al. | |
| 5,886,030 A | 3/1999 | Maniar | |
| 5,958,443 A | 9/1999 | Viegas et al. | |
| 6,074,580 A * | 6/2000 | Le Thiesse et al. | 264/14 |
| 6,274,634 B1 | 8/2001 | Yasueda et al. | |
| 6,432,439 B1 | 8/2002 | Suzuki et al. | |
| 6,455,547 B1 | 9/2002 | Kis | |
| 6,624,193 B1 | 9/2003 | Naka et al. | |

FOREIGN PATENT DOCUMENTS

| | | |
|---|---|---|
| EP | 0 995 435 | 4/2000 |
| JP | 2-256618 | 2/1990 |
| JP | 6-16556 | 1/1994 |
| JP | 11-21229 | 1/1999 |
| JP | H11-251538 | 9/2000 |
| WO | WO 98/51281 | 11/1998 |
| WO | WO 99/11239 | 3/1999 |
| WO | WO 01/17527 A1 | 3/2001 |

OTHER PUBLICATIONS

Toguchi et al., "Gastro-intestinal absorption of ethyl 2-Chloro-3[4-(2-methyl-2-phenylpropyloxy)phenyl]propionate from different dosage forms in rats and dogs." *Chem. Pharm. Bull.* 38:10(1990): 2792-2796.

* cited by examiner

*Primary Examiner* — Blessing M Fubara

(74) *Attorney, Agent, or Firm* — Hamre, Schumann, Mueller & Larson, P.C.

(57) ABSTRACT

Addition of polyvinylpyrrolidone and a water-soluble anionic macromolecular compound to an aqueous suspension of a hardly soluble drug allows to provide an aqueous suspension in which aggregation of drug particles, formation of macro crystals from suspended particles and formation of secondary particles from deposited particles are prevented, and adhesion and adsorption to containers made of plastics, e.g., polypropylene or polyethylene, are avoided. As it has a good redispersibility, the aqueous suspension is useful as eye drops, nasal drops, ear drops, injections, oral preparations, liniments and lotions.

9 Claims, No Drawings

AQUEOUS SUSPENSION PREPARATIONS

CROSS-REFERENCE TO RELATED APPLICATIONS

This application is a Divisional Application of 10/362,473, filed Feb. 24, 2003, which is a National Stage Application of PCT/JP2001/07128, filed Aug. 20, 2001, which claims benefit of Serial No. JP 2000-255000, filed Aug. 25, 2000 in Japan and which application(s) are incorporated herein by reference. A claim of priority to all, to the extent appropriate is made.

TECHNICAL FIELD

The present invention relates to an aqueous suspension with good redispersibility comprising polyvinylpyrrolidone and a water-soluble anionic macromolecular compound which are added to prevent a hardly soluble drug from adhering to a container and forming aggregates.

BACKGROUND ART

Aqueous suspensions often have problems such as difficulty in redispersion due to aggregation of drug particles, formation of macro crystals from suspended particles or formation of secondary particles from deposited particles, any of which could take place during long-term storage or when they are exposed to temporary heating or fluctuation of temperature/humidity. In addition, some types of suspended particles adhere to or get adsorbed by the walls of a plastic container and could thus cause a problem of unstable concentration of the drug contained in the aqueous suspensions.

To address these problems, measures have been taken in order to prevent formation of secondary particles by blocking sedimentation by reducing the size of the particles in suspension and increasing the viscosity of the dispersion medium with a water-soluble macromolecular compound, or to prevent aggregation of particles in the suspension by increasing the size of the particles in the suspension and thereby expanding the space between deposited particles. However, while it is not possible to completely prevent sedimentation of suspended particles by reducing the size of the particles in the suspension and increasing the viscosity of the dispersion medium, this measure could cause a problem by making it more difficult to redisperse particles which are once deposited from the suspension. On the other hand, increasing the size of particles in the suspension would cause problems such as foreign body sensation upon application or clogging of a container nozzle or a syringe needle.

In this situation, it is disclosed in Japanese Patent Application Publication H8-295622 that an aqueous suspension with good redispersibility can be obtained by addition of an ionic macromolecular compound such as carboxyvinyl polymer or carboxymethylcellulose and a metal cation such as sodium or potassium ion, and adjusting the viscosity to 100 cP. This method, however, cannot be used when high levels of viscosity is desired for improvement of the retention of a drug, because the redispersibility in this method is acquired by its low viscosity of 100 cP.

On the other hand, it is disclosed in EP0995435A1 (WO 98/51281) that an aqueous suspension with good redispersibility is obtained by addition of a water-soluble macromolecular compound within a concentration range from the concentration at which the surface tension of the aqueous suspension begins to decrease up to the concentration at which the reduction in the surface tension ceases. As it employs low concentrations of an aqueous macromolecular compound, this method cannot be used, either, when addition of higher concentrations of the macromolecular compound is needed for other reasons, e.g., for improvement of the retention of a drug.

Thus, there have been needs for an aqueous suspension with good redispersibility irrespective of its viscosity or of the amount of suspending and thickening agents such as water-soluble macromolecular compounds.

DISCLOSURE OF INVENTION

The objective of the present invention is to provide an aqueous suspension with good redispersibility.

As a result of studies performed to solve the above-mentioned problems, the inventors of the present invention surprisingly found that addition of polyvinylpyrrolidone and a water-soluble anionic macromolecular compound improves the redispersibility of hardly soluble drugs in an aqueous suspension, and completed the present invention based on the finding.

Thus, the present invention relates:

(1) An aqueous suspension comprising a hardly soluble drug, polyvinylpyrrolidone and a water-soluble anionic macromolecular compound, (2) the aqueous suspension defined above in (1), wherein the lower and the upper limit concentrations of polyvinylpyrrolidone are about 0.1 w/v % and about 10 w/v %, respectively, and the lower and the upper limit concentrations of the water-soluble anionic macromolecular compound are about 0.05 w/v % and about 1.0 w/v %, respectively, (3) the aqueous suspension defined above in (1), wherein the concentration of polyvinylpyrrolidone is 0.1-5.0 w/v % and the water-soluble anionic macromolecular compound is contained at a weight ratio of 0.1-2.0 to the amount of polyvinylpyrrolidone, (4) the aqueous suspension defined above in (2) or (3), wherein the hardly soluble drug is at least one selected from steroidal antiinflammatory drugs, antiphlogistic-analgesics, chemotherapeutics, synthetic antimicrobials, antivirals, hormones, anti-cataract drugs, neovascularization suppressants, immunosuppressants, protease inhibitors, aldose reductase inhibitors, antiallergics, anxiolytics, antipsychotics, antibiotics, antitumor drugs, anti-hyperlipemic drugs, antitussive-expectorants, muscle relaxants, antiepileptics, antiulcer drugs, antidepressants, cardiotonics, antiarrhythmic drugs, vasodilators, antihypertensive-diuretics, antidiabetics, antituberculosis drugs, narcotic antagonists, drugs for dermatologic diseases and diagnostic drugs, (5) the aqueous suspension defined above in (4), wherein the hardly soluble drug is a steroidal antiinflammatory drug, (6) the aqueous suspension defined above in (5), wherein the steroidal antiinflammatory drug is at least one selected from cortisone acetate, hydrocortisone acetate, betamethasone, prednisolone, fluticasone propionate, dexamethasone, triamcinolone, loteprednol, fluorometholone, difluprednate, mometasone furoate, clobetasol propionate, diflorasone diacetate, diflucortolone valerate, fluocinonide, amcinonide, halcinonide, fluocinolone acetonide, triamcinolone acetonide, flumethasone pivalate and clobetasone acetate, (7) the aqueous suspension defined above in (4), wherein the hardly soluble drug is an anti-cataract drug, (8) the aqueous suspension defined above in (7), wherein the anti-cataract drug is pirenoxine or N-(4-fluorophenylsulfonyl)-L-valyl-L-leucinal, (9) the aqueous suspension defined above in (4), wherein the hardly soluble drug is an antiphlogistic-analgesic,

(10) the aqueous suspension defined above in (9), wherein the antiphlogistic-analgesic is at least one selected from alclofenac, alminoprofen, indomethacin, epirizole, oxaprozin, ketoprofen, diclofenac sodium, diflunisal, naproxen, piroxicam, fenbufen, flufenamic acid, flurbiprofen, floctafenine, pentazocine, metiazinic acid, mefenamic acid, mofezolac, salicylic acid, sulpyrine, atropine, scopolamine, morphine, pethidine, levorphanol, oxymorphone and salts thereof,

(11) the aqueous suspension defined above in one of (1)-(10), wherein the water-soluble anionic macromolecular compound is at least one selected from anionic polysaccharides, anionic polyvinyl-based polymers and anionic macromolecular polypeptides,

(12) the aqueous suspension defined above in (11), wherein the anionic polysaccharide is at least one selected from carboxymethylcellulose or a salt thereof, alginic acid or a salt thereof, chondroitin sulfate or a salt thereof, pectin and xanthan gum,

(13) an aqueous suspension comprising a steroidal antiinflammatory drug, polyvinylpyrrolidone and alginic acid or a salt thereof,

(14) the aqueous suspension defined above in (11), wherein the lower and the upper limit concentrations of polyvinylpyrrolidone are about 0.1 w/v % and about 10 w/v %, respectively, and the lower and the upper limit concentrations of alginic acid or a salt thereof are about 0.05 w/v % and about 1.0 w/v %, respectively,

(15) an aqueous suspension comprising an anti-cataract drug, polyvinylpyrrolidone and alginic acid or a salt thereof,

(16) the aqueous suspension defined above in (15), wherein the lower and the upper concentrations of polyvinylpyrrolidone are about 0.1 w/v % and about 10 w/v %, respectively, and the lower and the upper limit concentrations of alginic acid or a salt thereof are about 0.05 w/v % and about 1.0 w/v %, respectively,

(17) the aqueous suspension defined above in (16), wherein the anti-cataract drug is pirenoxine,

(18) an aqueous suspension comprising an antiphlogistic-analgesic, polyvinylpyrrolidone and alginic acid or a salt thereof,

(19) the aqueous suspension defined above in (18), wherein the lower and the upper concentrations of polyvinylpyrrolidone are about 0.1 w/v % and about 10 w/v %, respectively, and the lower and the upper limit concentrations of alginic acid or a salt thereof are about 0.2 w/v % and about 1.0 w/v %, respectively,

(20) the aqueous suspension defined above in one of (1)-(19), wherein the aqueous suspension is in the form of eye drops,

(21) the aqueous suspension defined above in one of (1)-(19), wherein the aqueous suspension is in the form of nasal drops,

(22) the aqueous suspension defined above in one of (1)-(19), wherein the aqueous suspension is in the form of ear drops,

(23) the aqueous suspension defined above in one of (1)-(19), wherein the aqueous suspension is in the form of an injection,

(24) the aqueous suspension defined above in one of (1)-(19), wherein the aqueous suspension is in the form of an oral preparation,

(25) the aqueous suspension defined above in one of (1)-(19), wherein the aqueous suspension is in the form of a liniment,

(26) the aqueous suspension defined above in one of (1)-(19), wherein the aqueous suspension is in the form of a lotion,

(27) a method for improving the redispersibility of an aqueous suspension of a hardly soluble drug comprising addition of polyvinylpyrrolidone and a water-soluble anionic macromolecular compound to the aqueous suspension,

(28) the method defined above in (27), wherein the lower and the upper concentrations of polyvinylpyrrolidone are about 0.1 w/v % and about 10 w/v %, respectively, and the lower and the upper limit concentrations of the water-soluble anionic macromolecular compound are about 0.05 w/v % and about 1.0 w/v %, respectively, and

(29) the method defined above in (27), wherein the concentration of polyvinylpyrrolidone is 0.1-5.0 w/v % and the water-soluble anionic macromolecular compound is contained at a weight ratio of 0.1-2.0 to the amount of polyvinylpyrrolidone.

Examples of polyvinylpyrrolidone (INN: povidon) used in the present invention include, e.g., polyvinylpyrrolidone K15 (K: intrinsic viscosity, i.e., Fikentscher's K-Value), polyvinylpyrrolidone K17, polyvinylpyrrolidone K25, polyvinylpyrrolidone K30, polyvinylpyrrolidone K60 and polyvinylpyrrolidone K90, among which polyvinylpyrrolidone K25 and polyvinylpyrrolidone K30 are preferable.

Examples of anionic polysaccharides which are within the scope of the water-soluble anionic macromolecular compounds used in the present invention include carboxymethylcellulose and salts thereof, alginic acid and salts thereof, chondroitin sulfate and salts thereof, pectin and xanthan gum. Examples of salts of carboxymethylcellulose include sodium salt and calcium salt. Examples of salts of alginic acid include sodium salt, potassium salt, calcium salt, and sodium-calcium salt. Examples of salts of chondroitin sulfate include sodium salt, potassium salt and calcium salt. Carboxymethylcellulose and salts thereof or alginic acid and salts thereof are preferred, among which sodium alginate is particularly preferred.

Examples of anionic polyvinyl-based polymers which are within the scope of the water-soluble anionic macromolecular compounds used in the present invention include carboxyvinyl polymers.

Example of anionic macromolecular polypeptides which are within the scope of the water-soluble anionic macromolecular compounds used in the present invention include gelatin (type B).

The concentration of polyvinylpyrrolidone may be determined as desired between the lower limit of about 0.1 w/v %, preferably about 0.3 w/v % and the upper limit of about 10 w/v %, preferably about 5 w/v %, more preferably about 2 w/v %. The concentration of a water-soluble anionic macromolecular compound may be determined as desired between the lower limit of about 0.05 w/v %, preferably about 0.1 w/v %, more preferably about 0.2 w/v % and the upper limit, which is lower than those concentrations that trigger gel formation, specifically about 1.0 w/v %, preferably about 0.5 w/v %.

As for a water-soluble anionic macromolecular compound, it is preferably contained at a weight ratio of from about 0.01 to about 2.0 to the weight of polyvinylpyrrolidone when the concentration of polyvinylpyrrolidone is from about 0.1 to about 10 w/v %, and more preferably at a weight ratio of 0.1-2.0 to the weight of polyvinylpyrrolidone when the concentration of polyvinylpyrrolidone is 0.1-5.0 w/v %.

Examples of hardly soluble drugs used in the present invention may be those which exhibit solubility as defined by any of the terms, "sparingly soluble", "slightly soluble", "very slightly soluble" and "practically insoluble" set forth in the Japanese Pharmacopoeia, and any drugs are included which could be provided as aqueous suspensions in their final forms.

Examples of hardly soluble drugs used in the present invention include steroidal antiinflammatory drugs, antiphlogistic-analgesics, chemotherapeutics, synthetic antimicrobials, antivirals, hormones, anti-cataract drugs, neovascularization suppressants, immunosuppressants, protease inhibitors, aldose reductase inhibitors, antiallergics, anxiolytics, antipsychotics, antibiotics, antitumor drugs, anti-hyperlipemic drugs, antitussive-expectorants, muscle relaxants, antiepileptics, antiulcer drugs, antidepressants, cardiotonics, antiarrhythmic drugs, vasodilators, antihypertensive-diuretics, antidiabetics, antituberculosis drugs, narcotic antagonists, drugs for dermatologic diseases and diagnostic drugs, among which steroidal antiinflammatory drugs, antiphlogistic-analgesics and anti-cataract drugs are preferred. Examples of steroidal antiinflammatory drugs include cortisone acetate, hydrocortisone acetate, betamethasone, prednisolone, fluticasone propionate, dexamethasone, triamcinolone, loteprednol, fluorometholone, difluprednate, momethasone furoate, clobetasol propionate, diflorasone diacetate, diflucortolone valerate, fluocinonide, amcinonide, halcinonide, fluocinolone acetonide, triamcinolone acetonide, flumethasone pivalate and clobetasone acetate, among which fluorometholone is preferred. Examples of antiphlogistic-analgesics include alclofenac, alminoprofen, indomethacin, epirizole, oxaprozin, ketoprofen, diclofenac sodium, diflunisal, naproxen, piroxicam, fenbufen, flufenamic acid, flurbiprofen, floctafenine, pentazocine, metiazinic acid, mefenamic acid, mofezolac, salicylic acid, sulpyrine, atropine, scopolamine, morphine, pethidine, levorphanol, oxymorphone and salts thereof, among which indomethacin is preferred. Examples of chemotherapeutics include sulfonamide antimicrobials such as salazosulfapyridine, sulfadimethoxine, sulfamethizole, sulfamethoxazole, sulfamethopyrazine and sulfamonomethoxine; synthetic antimicrobials such as enoxacin, ofloxacin, cinoxacin, sparfloxacin, thiamphenicol, nalidixic acid, tosufloxacin tosilate, norfloxacin, pipemidic acid trihydrate, piromidic acid, fleroxacin, revofloxacin; antivirals such as acyclovir, ganciclovir, didanosine, zidovudine, nevirapine, vidarabine, nelfinavir mesilate and ritonavir; antifungal agents such as itraconazole, ketoconazole, fluconazole, flucytosine, miconazole and pimaricin. Examples of hormones include insulin zinc, testosterone propionate, estradiol benzoate, methimazole and estriol. Examples of anti-cataract drugs include pirenoxine and N-(4-fluorophenylsulfonyl)-L-1-valyl-L-leucinal. Examples of neovascularization suppressants include fumagillin and derivatives thereof. Examples of immunosuppressants include cyclosporine, rapamycin and taclorimus. Examples of protease inhibitors include [L-3-trans-ethoxycarbonyloxysilane-2-carbonyl]-L-leucine(3-methylbutyl)amide (E-64-d). Examples of aldose reductase inhibitors include 5-(3-ethoxy-4-pentyloxyphenyl) thiazolidine-2,4-dione. Examples of antiallergics include tranilast, clemastine fumarate, mequitazine, diphenhydramine, chlorpheniramine, tripelennamine, methdilazine, clemizole, diphenylpyraline and methoxyphenamine. Examples of anxiolytics include diazepam, lorazepam and oxazepam. Examples of antipsychotics include chlorpromazine, prochlorperazine and trifluperazine. Examples of antibiotics include gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephaloridine, cefotiam, cefotiam hexetil, cefsulodin, cefmenoxime, cefmetazole, cefazolin, cefotaxime, cefoperazone, ceftizoxime, moxalactam, thienamycin, sulfazecin, azthreonam and salts thereof. Examples of antitumor drugs include 6-O—(N-chloroacetylcarbamoyl)fumagilol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon and glycyrrhizin. Examples of anti-hyperlipemic drugs include clofibrate and 2-chloro-3-[4-(2-methyl-2-phenylpropoxy)phenyl]propionic acid ethyl ester [Chemical And Pharmaceutical Bulletin (Chem. Pharm. Bull.), 38, 2792-2796 (1990)]. Examples of antitussive-expectorants include ephedrine, methylephedrine, noscapine, codeine, dihydrocodeine, alloclamide, chlorphedianol, picoperidamine, chloperastine, protokylol, isoproterenol, salbutamol, terbutaline, and salts thereof. Examples of muscle relaxants include pridinol, tubocurarine and pancuronium. Examples of antiepileptics include phenitoin, ethosuccimide, acetazolamide and chlordiazepoxide. Examples of antiulcer drugs include synthetic aluminum silicate, aldioxa, lansoprazole and metoclopramide. Examples of antidepressants include imipramine, clomipramine, noxiptyline and phenelzine. Examples of cardiotonics include trans-π-oxocamphor, terephylol, aminophylline and etilefrine. Examples of antiarrhythmic drugs include propranolol, alprenolol, bufetolol and oxprenolol. Examples of vasodilators include oxyephedrine, diltiazem, tolazoline, hexobendine and bamethane. Examples of antihypertensive-diuretics include hexamethonium bromide, pentolinium, mecamylamine, ecarazine, clonidine, diltiazem and nifedipine. Examples of antidiabetics include glymidine, glipzide, fenformine, buformin and metformine. Examples of antituberculosis drugs include isoniazid, ethambutol, para-aminosalicylic acid. Examples of narcotic antagonists include levallorphan, nalorphine, naloxone and salts thereof. Examples of drugs for dermatologic diseases include calamine and sulfur. Examples of diagnostic drugs include barium sulfate.

The concentrations of a hardly soluble drug in the present invention may be determined depending on the drug employed, the intended purpose and the way of application. For example, fluorometholone, a steroidal antiinflammatory drug, may be prepared at a concentration of from about 0.02 to about 0.1 w/v % when used in the form of suspension-type eye drops for allergic conjunctivitis. Indomethacin, an antiphlogistic-analgesic, may be prepared at a concentration of from about 0.1 to about 1.0 w/v % when used in the form of suspension-type eye drops for postoperative inflammation. Pirenoxine, an anti-cataract drug, may be prepared at a concentration of from about 0.001 to about 0.01 w/v % when used in the form of suspension-type eye drops for the incipient stage of senile cataract. Eye drops may be applied 3-5 times a day, 1-2 drops at a time. As to betamethasone, a steroidal antiinflammatory drug, when it is intravenously injected in the form of a suspension-type injection for rheumatic fever, it may be prepared at a concentration of from about 0.4 to about 2.0 w/v % and administered in an amount of about 2-8 mg at a time and at intervals of 3-6 hours. When it is used in the form of a suspension-type oral preparation for rheumatoid arthritis, it may be prepared at a concentration of from about 0.01 to about 0.05 w/v % and administered 1-4 times a day, with a daily dose being from about 0.5 to about 8 mg. Also, when it is used in the form of a suspension-type lotion for allergic eczema, it may be prepared at a concentration of from about 0.06 to about 0.12 w/v % and applied from one to several times a day.

As to the relation between a hardly soluble drug and the concentrations of polyvinylpyrrolidone and a water-soluble anionic macromolecular compound in the aqueous suspension of the present invention, polyvinylpyrrolidone and a water-soluble anionic macromolecular compound may be used as desired within the concentration ranges described hereinbefore, regardless of which hardly soluble drug is selected. Their particularly preferable concentration ranges when used with a steroidal antiinflammatory drug, for example, are defined by the lower and the upper limit concentrations of about 0.1 w/v % and about 10 w/v %, respectively, for polyvinylpyrrolidone and by the lower and the upper limit concentrations of about 0.05 w/v % and about 1.0 w/v %, respectively, for alginic acid or salts thereof. When used with an anti-cataract drug, such ranges are defined by the lower and the upper limit concentrations of about 0.1 w/v % and about 10 w/v %, respectively, for polyvinylpyrrolidone and by the lower and the upper limit concentrations of about 0.05 w/v % and about 1.0 w/v %, respectively, for alginic acid or salts thereof. When used with an antiphlogistic-analgesic, it is preferable that the lower and the upper limit concentrations of polyvinylpyrrolidone are about 0.1 w/v % and about 10 w/v %, respectively, and that the lower and the upper limit concentrations of alginic acid or salts thereof are about 0.2 w/v % and about 1.0 w/v %, respectively.

In addition to a hardly soluble drug, polyvinylpyrrolidone and a water-soluble anionic macromolecular compound, the aqueous suspension of the present invention may further contain, as desired, for example, isotonizers (sodium chloride, potassium chloride, glycerol, mannitol, sorbitol, boric acid, borax, glucose, propylene glycol, etc.), buffers (phosphate buffer, acetate buffer, borate buffer, carbonate buffer, citrate buffer, tris buffer, glutamic acid, ε-aminocaproic acid, sodium acetate, boric acid, borax, etc.), preservatives (chlorobutanol, benzyl alcohol, sodium dehydroacetate, sodium edetate, benzalkonium chloride, benzethonium chloride, methyl p-hydroxybenzoate, ethyl p-hydroxybenzoate, propyl p-hydroxybenzoate, boric acid, borax, etc.), thickening agents (hydroxyethylcellulose, hydroxypropylcellulose, hydroxypropylmethylcellulose, polyvinylalcohol, polyethylene glycol, etc.) surfactants (polysorbate 80, polyoxyethylene hydrogenated castor oil, tyloxapol, polyethylene glycol monostearate, sucrose fatty acid ester, etc.), stabilizers (sodium hydrogen sulfite, sodium thiosulfate, sodium edetate, sodium citrate, sodium acetate, ascorbic acid, dibutylhydroxytoluene, boric acid, borax, etc.), topical astringents (zinc oxide, bismuth subgallate, etc.), topical antiphlogistic-analgesics (d-camphor, dl-camphor, dl-menthol, etc.), dispersion stabilizers (bentonite, tragacanth, gum arabic, gelatin, etc.), pH adjusting agents (hydrochloric acid, sodium hydroxide, phosphoric acid, acetic acid, etc.), flavoring agents (simple syrup, lactose, glucose, honey, bitter tincture, etc.), sweetening agents (fructose, xylitol, sorbitol, simple syrup, lactose, etc.) and aromatic substances (orange oil, spearmint oil, lemon oil, rose oil, menthol, peppermint oil, etc.).

Though the amount of these additives may be determined depending on which additives are chosen, and on their intended use, they may be added at concentrations that allows to accomplish the purpose of their addition. Thus, for example, an isotonizer may usually be added at a concentration of from about 0.5 to about 5.0 w/v % to give an osmotic pressures of from about 229 to about 343 mOs/Kg·H$_2$O. Likewise, a buffer may generally be added at a concentration of from about 0.01 to about 2.0 w/v %, and a thickening agent, from about 0.01 to about 1.0 w/v %, a surfactant, from about 0.01 to about 10.0 w/v %, and a stabilizer, from about 0.001 to about 1.0 w/v %. A pH adjusting agent may be added as desired to adjust the pH to a value of from about 3 to about 9, preferably from about 4 to about 8.

The excellent redispersibility of the aqueous suspension of the present invention allows itself to be used as a medicament (e.g., drugs for prophylaxis or treatment of various diseases) for a human and as a veterinary drug for other mammalian animals (e.g., rats, mice, guinea pigs, monkeys, dogs, bovines, pigs, etc.).

The aqueous suspension of the present invention may be used in the forms of eye drops, nasal drops, ear drops, an injection, an oral liquid preparation, a liniment and a lotion, among which eye drops are especially preferred.

BEST MODE FOR CARRYING OUT THE INVENTION

The present invention is described in further detail below with reference to the test examples and the working examples.

TEST EXAMPLE 1

Redispersibility Test

Test Methods 0.1 w/v % fluorometholone suspensions containing polyvinylpyrrolidone K25 and sodium alginate at different concentrations were filled in polypropylene and polyethylene containers, kept at about 60° C. for about 18 hours, and their appearance and redispersibility then were examined.

Test Results

The results are shown in Table 1.

TABLE 1

Results of redispersibility test of fluorometholone suspensions

| | | Sodium alginate (w/v %) | | | | | | | |
|---|---|---|---|---|---|---|---|---|---|
| | | 0 | | 0.1 | | 0.3 | | 0.5 | |
| | | PP | PE | PP | PE | PP | PE | PP | PE |
| PVP | 0.1 | X | X | — | — | — | — | — | — |
| (w/v %) | 0.3 | X | X | ○ | ⊚ | ○ | ⊚ | ○ | ⊚ |
| | 0.5 | X | X | ○ | ⊚ | ○ | ⊚ | ○ | ⊚ |
| | 1.0 | X | X | ○ | ⊚ | ○ | ⊚ | ○ | ⊚ |

PVP: polyvinylpyrrolidone K25
PP: polypropylene containers
PE: polyethylene containers In the table, x indicates that particles of fluorometholone adhered to the container and they did not redisperse even after being subjected to rotation of more than 100 rounds at 40 rpm on a variable mix rotor VMR-5 (mfd. by IUCHISEIEIDO).

In the table, ○ indicates that the particles of fluorometholone settled down but redispersed after being subjected to rotation of 25-40 rounds at 40 rpm on a variable mix rotor VMR-5 (mfd. by IUCHISEIEIDO).

In the table, ⊚ indicates that the particles of fluorometholone settled down but redispersed simply by inverting the container.

In the fluorometholone suspensions to which was added polyvinylpyrrolidone alone, aggregation occurred and the particles, which adhered to the container, did not redisperse. In the fluorometholone suspension to which were added polyvinylpyrrolidone and sodium alginate, the particles showed no adhesion to the container and redispersed.

TEST EXAMPLE 2

Redispersibility Test

Test Methods 0.1 w/v % fluorometholone suspensions containing polyvinylpyrrolidone K25 and sodium alginate at different concentrations were filled in polypropylene containers. After storage for about 18 hours at about 60° C., the containers were repeatedly inverted and the number of times of the inversion was counted until the suspended particles redispersed and became non-adhesive to the container.

Test Results

The results are shown in Table 2. Good redispersion of fluorometholone was observed with 0.1 w/v % or more polyvinylpyrrolidone (K25) and 0.05 w/v % or more sodium alginate. In contrast, in the preparations containing 0.2 w/v % sodium alginate but no polyvinylpyrrolidone (K25), fluorometholone floated on the surface of the aqueous solution and no homogeneous suspension was obtained. The floating fluorometholone aggregated with the lapse of time.

Test examples 1 and 2 revealed that at least certain concentrations of polyvinylpyrrolidone and sodium alginate are both essential for the present invention.

TABLE 2

Results of redispersibility test of fluorometholone suspensions

| | | Sodium alginate (w/v %) | | | | | |
|---|---|---|---|---|---|---|---|
| | | 0.01 | 0.03 | 0.05 | 0.075 | 0.1 | 0.2 |
| PVP (w/v %) | 0 | — | — | — | — | — | X |
| | 0.1 | — | — | — | — | ○ (10 times) | — |
| | 1.0 | X | X | ○ (thrice) | ○ (twice) | — | — |
| | 2.0 | — | — | — | — | ○ (once) | — |
| | 5.0 | — | — | — | — | ○ (once) | — |
| | 10.0 | — | — | — | — | ○ (once) | — |

PVP: polyvinylpyrrolidone K25

In the table, x indicates that the particles of fluorometholone adhered to the container and did not redisperse.

In the table, ○ indicates that the particles of fluorometholone redispersed after inversion repeated the number of times indicated in the parentheses.

TEST EXAMPLE 3

Redispersibility Test

Test Methods

To a 0.005 w/v % of pirenoxine suspension containing 1.0 w/v % of polyvinylpyrrolidone K30 was added sodium alginate at different concentrations, and the mixtures were filled in polypropylene and polyethylene containers. After storage for about 18 hours at about 60° C., the containers were repeatedly inverted and the number of times of the inversion was counted until the suspended particles redispersed and became non-adhesive to the container.

The formulae of the pirenoxine suspension are shown in Table 3.

TABLE 3

Formulae of pirenoxine suspensions

| Formula Nos. | P-0 | P-1 | P-5 |
|---|---|---|---|
| Pirenoxine | 0.005 g | 0.005 g | 0.005 g |
| Polyvinylpyrrolidone K30 | 1.0 g | 1.0 g | 1.0 g |
| Sodium alginate | — | 0.1 g | 0.5 g |
| Hydrochloric acid | q.s. | q.s. | q.s. |
| Sodium hydroxide | q.s. | q.s. | q.s. |
| Purified water | q.s. | q.s. | q.s. |
| Total amount | 100 mL | 100 mL | 100 mL |
| pH | 4.0 | 4.0 | 4.0 |

Test Results

The results are shown in Table 4.

TABLE 4

Results of redispersibility test of pirenoxine suspensions

| | Formula Nos. | | |
|---|---|---|---|
| | P-0 | P-1 | P-5 |
| Polypropylene containers | x | ○ (thrice) | ○ (once) |
| Polyethylene containers | x | ○ (twice) | ○ (once) |

In the table, x indicates that the particles of pirenoxine adhered to the containers and did not redisperse.

In the table, ○ indicates that the particles of pirenoxine redispersed after inversion repeated the number of times indicated in the parentheses.

In the pirenoxine suspension to which polyvinylpyrrolidone (K30) alone was added, aggregation occurred in either containers, and the particles did not redisperse and remained adhering to the containers. In the pirenoxine suspension to which polyvinylpyrrolidone (K30) and sodium alginate were added, particles did not adhere to the container and redispersed after a few times of inversion.

TEST EXAMPLE 4

Redispersibility Test

Test Method

To a 0.5 w/v % of indomethacin suspension containing 1.0 w/v % of polyvinylpyrrolidone K30 was added sodium alginate at different concentrations, and the mixtures were filled in polypropylene and polyethylene containers. After storage for about 18 hours at about 60° C., the containers were repeatedly inverted and the number of times of the inversion was counted until the suspended particles redispersed and became non-adhesive to the container.

The formulae of the indomethacin suspensions are shown in Table 5.

TABLE 5

Formulae of indomethacin suspensions

| | Formula Nos. | | | | | |
|---|---|---|---|---|---|---|
| | I-0 | I-1 | I-2 | I-3 | I-4 | I-5 |
| Indomethacin | 0.5 g | 0.5 g | 0.5 g | 0.5 g | 0.5 g | 0.5 g |
| Sodium acetate | 0.1 g | 0.1 g | 0.1 g | 0.1 g | 0.1 g | 0.1 g |
| Polyvinylpyrrolidone K30 | 1.0 g | 1.0 g | 1.0 g | 1.0 g | 1.0 g | 1.0 g |
| Sodium alginate | — | 0.1 g | 0.2 g | 0.3 g | 0.4 g | 0.5 g |
| Hydrochloric acid | q.s. | q.s. | q.s. | q.s. | q.s. | q.s. |
| Sodium hydroxide | q.s. | q.s. | q.s. | q.s. | q.s. | q.s. |
| Purified water | q.s. | q.s. | q.s. | q.s. | q.s. | q.s. |
| Total amount | 100 mL | 100 mL | 100 mL | 100 mL | 100 mL | 100 mL |
| pH | 5.0 | 5.0 | 5.0 | 5.0 | 5.0 | 5.0 |

Test Results

The results are shown in Table 6.

TABLE 6

Results of redispersibility test of indomethacin suspensions

| | Formula Nos. | | | | | |
|---|---|---|---|---|---|---|
| | I-0 | I-1 | I-2 | I-3 | I-4 | I-5 |
| Polypropylene containers | X | Δ | ○ (9 times) | ○ (5 times) | ○ (5 times) | ○ (5 times) |
| Polyethylene containers | ○ (10 times) | ○ (thrice) | — | — | — | ○ (twice) |

In the table, x indicates that the particles of indomethacin adhered to the containers and did not redisperse.

In the table, ○ indicates that the particles of indomethacin redispersed after inversion repeated the number of times indicated in the parentheses.

In the table, Δ indicates that the particles of indomethacin adhered to the containers in two cases in the triplicate experiment and did not redisperse, but redispersed in one case after inversion of 12 times.

The indomethacin suspensions showed container-dependency. Their redispersibility in the polypropylene containers was improved with sodium alginate at concentrations equal to or higher than 0.2 w/v %. In polyethylene containers, redispersibility was improved with polyvinylpyrrolidone (K30) alone, but further improved with polyvinylpyrrolidone (K30) and sodium alginate.

The above results revealed that hardly soluble drugs can be made into suspensions with good redispersibility by addition of polyvinylpyrrolidone and an water-soluble anionic macromolecular compound.

EXAMPLE 1

| Eye drops | |
|---|---|
| Fluorometholone | 0.1 g |
| Sodium dihydrogen phosphate, dihydrate | 0.1 g |
| Sodium chloride | 0.8 g |
| Polyvinylpyrrolidone K25 | 0.5 g |
| Sodium alginate | 0.2 g |
| Polysorbate 80 | 0.1 g |

-continued

| Eye drops | |
|---|---|
| Benzalkonium chloride | 0.005 g |
| Sodium hydroxide | q.s. |
| Purified water | to 100 mL |
| pH | 7.0 |

Sodium dihydrogen phosphate, dihydrate, sodium chloride, polysorbate 80, polyvinylpyrrolidone K25, sodium alginate and benzalkonium chloride were added to about 80 mL of purified water and dissolved, and the pH was adjusted to 7 with sodium hydroxide. Fluorometholone then was added and homogeneously suspended with a homogenizer. Addition of purified water to make the total volume of 100 mL gave suspension-type eye drops containing fluorometholone.

EXAMPLE 2

| Eye drops | |
|---|---|
| Indomethacin | 0.5 g |
| Sodium acetate | 0.1 g |
| Sodium chloride | 0.8 g |
| Polyvinylpyrrolidone K30 | 1.0 g |
| Sodium alginate | 0.5 g |
| Methyl p-hydroxybenzoate | 0.026 g |
| Propyl p-hydroxybenzoate | 0.014 g |
| Hydrochloric acid | q.s. |
| Purified water | to 100 mL |
| pH | 5.0 |

Sodium acetate, sodium chloride, polyvinylpyrrolidone K30, sodium alginate, methyl p-hydroxybenzoate and propyl p-hydroxybenzoate were added to about 80 mL of purified water and dissolved. Indomethacin then was added and homogeneously suspended with a homogenizer, and the pH was adjusted to 5 with hydrochloric acid. Addition of purified water to make the total volume of 100 mL gave suspension-type eye drops containing indomethacin.

EXAMPLE 3

| Eye drops | |
|---|---|
| Pirenoxine | 0.005 g |

| Eye drops | |
|---|---|
| Sodium acetate | 0.1 g |
| Sodium chloride | 0.8 g |
| Polyvinylpyrrolidone K30 | 1.0 g |
| Sodium alginate | 0.1 g |
| Benzalkonium chloride | 0.005 g |
| Hydrochloric acid | q.s. |
| Purified water | to 100 mL |
| pH | 4.0 |

Sodium acetate, sodium chloride, polyvinylpyrrolidone K30, sodium alginate and benzalkonium chloride were added to about 80 mL of purified water and dissolved. Pirenoxine then was added and homogeneously suspended with a homogenizer, and the pH was adjusted to 4 with hydrochloric acid. Addition of purified water to make the total volume of 100 mL gave suspension-type eye drops containing pirenoxine.

EXAMPLE 4

| Nasal drops | |
|---|---|
| Dexamethasone | 0.1 g |
| Sodium chloride | 0.5 g |
| Polyvinylpyrrolidone K25 | 1.0 g |
| Sodium alginate | 0.2 g |
| Boric acid | 0.7 g |
| Borax | q.s. |
| Sodium edetate | 0.0005 g |
| Benzalkonium chloride | 0.0005 g |
| Sodium chloride/hydrochloric acid | q.s. |
| Purified water | to 100 mL |
| pH | 7.0 |

Sodium chloride, polyvinylpyrrolidone K25, sodium alginate, boric acid, borax, sodium edetate and benzalkonium chloride are added to about 80 mL of purified water and dissolved. Dexamethasone then are added and homogeneously suspended with a homogenizer, and the pH is adjusted to 7 with sodium hydroxide/hydrochloric acid. Addition of purified water to make the total volume of 100 mL gives suspension-type nasal drops containing dexamethasone.

EXAMPLE 5

| Ear drops | |
|---|---|
| Fradiomycin | 1.0 g |
| Boric acid | 0.7 g |
| Borax | q.s. |
| Sodium chloride | 0.5 g |
| Polyvinylpyrrolidone K30 | 0.5 g |
| Sodium carboxymethylcellulose | 0.1 g |
| Purified water | to 100 mL |
| pH | 6.5 |

Boric acid, sodium chloride, polyvinylpyrrolidone K30 and carboxymethylcellulose are added to about 80 mL of purified water and dissolved. After borax is dissolved and pH adjusted to 6.5, fradiomycin is added and homogeneously suspended with a homogenizer. Addition of purified water to make the total volume of 100 mL gives suspension-type ear drops containing fradiomycin.

EXAMPLE 6

| Injection | |
|---|---|
| Betamethasone | 0.8 g |
| Polyvinylpyrrolidone K25 | 0.5 g |
| Sodium carboxymethylcellulose | 0.5 g |
| Polysorbate 80 | 0.01 g |
| Benzalkonium chloride | 0.02 g |
| Sodium hydroxide/hydrochloric acid | q.s. |
| Purified water | to 100 mL |
| pH | 7.0 |

Polyvinylpyrrolidone K25, sodium carboxymethylcellulose, polysorbate 80 and benzalkonium chloride are added to about 80 mL of purified water and dissolved. Betamethasone then is added and homogeneously suspended with a homogenizer, and the pH is adjusted to 7 with sodium hydroxide/hydrochloric acid. Addition of purified water to make the total volume of 100 mL gives a suspension-type injection containing betamethasone.

EXAMPLE 7

| Injection | |
|---|---|
| Estradiol benzoate | 0.1 g |
| Polyvinylpyrrolidone K30 | 0.5 g |
| Sodium alginate | 0.5 g |
| Ethyl p-hydroxybenzoate | 0.05 g |
| Sodium hydroxide/hydrochloric acid | q.s. |
| Purified water | to 100 mL |
| pH | 6.5 |

Polyvinylpyrrolidone K30, sodium alginate and ethyl p-hydroxybenzoate are added to about 80 mL of purified water and dissolved. Estradiol benzoate then is added and homogeneously suspended with a homogenizer, and the pH adjusted to 6.5 with sodium hydroxide/hydrochloric acid. Addition of purified water to make the total volume of 100 mL gives a suspension-type injection containing estradiol benzoate.

EXAMPLE 8

| Oral suspension | |
|---|---|
| Synthetic aluminum silicate | 5.0 g |
| Aluminum oxide | 1.2 g |
| Bitter tincture | 2.0 mL |
| Polyvinylpyrrolidone K30 | 1.0 g |
| Sodium alginate | 0.2 g |
| Simple syrup | 8.0 mL |
| Purified water | to 100 mL |

Glycerol, polyvinylpyrrolidone K30, sodium alginate and simple syrup are added to about 80 mL of purified water and dissolved. Synthetic aluminum silicate, aluminum oxide and bitter tincture then are added and homogeneously suspended with a homogenizer. Addition of water to make the total volume of 100 mL gives an oral suspension containing synthetic aluminum silicate.

EXAMPLE 9

| Calamine lotion | |
| --- | --- |
| Calamine | 8.0 g |
| Zinc oxide | 8.0 g |
| Glycerol | 2.0 mL |
| Polyvinylpyrrolidone K30 | 0.5 g |
| Carboxymethylcellulose | 0.2 g |
| Bentonite | 2.0 g |
| Purified water | 40.0 mL |
| Limewater | to 100 mL |

Glycerol, polyvinylpyrrolidone K30 and carboxymethylcellulose are added to 40 mL of purified water and dissolved. Calamine, zinc oxide and bentonite then are added and homogeneously suspended with a homogenizer. Addition of limewater to make the total volume of 100 mL and re-homogenization with a homogenizer gives a calamine lotion.

INDUSTRIAL APPLICABILITY

The aqueous suspension of the present invention prevents aggregation of drug particles, formation of macro crystal from suspended particles and formation of secondary particles from deposited particles, and blocks adhesion and adsorption to containers made of plastics such as polypropylene or polyethylene, and provides good redispersibility. It therefore can be used as a good aqueous suspension in the forms of eye drops, nasal drops, nasal drops, an injection, an oral preparation, a liniment, a lotion, etc.

The present invention is described above in detail with reference to a limited number of specific embodiments. As it would be possible for those skilled in the art to make various changes and modifications to the above-described specific embodiments without substantially departing from the scope of the novel teachings and advantages provided by the present invention, the all of such changes and modifications are also included within the spirit and scope of the present invention which is defined by the appended claims.

The present invention is based on Japanese Patent Application No. 2000-255000, the entire content of which is included in the present description.

The invention claimed is:

1. A method for improving redispersibility of an aqueous suspension of a hardly soluble drug, comprising:
    adding a hardly soluble drug to an aqueous medium comprising about 0.1 w/v % to about 10 w/v % polyvinylpyrrolidone and about 0.05 w/v % to about 1.0 w/v % anionic polysaccharide selected from the group consisting of alginic acid and salts thereof, chondroitin sulfate and salts thereof, pectin, and xanthan gum; and
    mixing the hardly soluble drug with the aqueous medium to form an aqueous suspension of the hardly soluble drug, wherein the suspension exhibits reduced adherence or absorption of the hardly soluble drug to plastic and the hardly soluble drug redisperses into the suspension with agitation.

2. The method according to claim 1, wherein the concentration of polyvinylpyrrolidone is 0.1-5.0 w/v %.

3. The method of claim 1, wherein the anionic polysaccharide comprises alginic acid or a salt thereof.

4. The method of claim 1, wherein the agitation comprises inversion.

5. The method of claim 1, wherein the agitation comprises rotation of 25-40 rounds at 40 rpm on a variable mix rotor.

6. The method of claim 1, wherein the plastic is polypropylene.

7. The method of claim 1, wherein the plastic is polyethylene.

8. The method of claim 1, wherein the hardly soluble drug comprises fluorometholone, pirenoxine, indomethacin, dexamethasone, fradiomycin, betamethasone, or estradiol benzoate.

9. The method of claim 1, wherein the aqueous medium comprises about 0.1 w/v % to about 10 w/v % polyvinylpyrrolidone and about 0.05 w/v % to about 0.5 w/v % anionic polysaccharide.

* * * * *